United States Patent [19]

Hurka et al.

[11] Patent Number: 4,841,964
[45] Date of Patent: Jun. 27, 1989

[54] INHALER

[76] Inventors: Wilhelm Hurka, Am Pfarrfeld 1, A9851 Lieserbrücke, Austria; Rudolf A. Hatschek, 3, rue Jacques-Vogt, Fribourg 5, Switzerland, CH-1700

[21] Appl. No.: 892,197

[22] Filed: Jul. 31, 1986

[30] Foreign Application Priority Data

Aug. 1, 1985 [AT] Austria ................................ 2272/85

[51] Int. Cl.$^4$ ............................................. A61M 16/00
[52] U.S. Cl. ........................... 128/203.15; 128/203.23; 604/58
[58] Field of Search ....................... 128/203.15, 203.23; 604/57, 58; 222/224

[56] References Cited

U.S. PATENT DOCUMENTS

| | | | |
|---|---|---|---|
| 2,534,636 | 12/1950 | Stirn | 128/203.15 |
| 2,816,549 | 12/1957 | Webster | 128/203.15 |
| 3,809,084 | 5/1974 | Hansen | 128/203.15 |

Primary Examiner—Edward M. Coven
Assistant Examiner—K. M. Reichle
Attorney, Agent, or Firm—Kurt Kelman

[57] ABSTRACT

An inhaler is described for introducing a solid substance in particulate form into the inhaled air of a user. The inhaler comprises a body in which is provided an endless orbital path 3 for one or more balls 4. Air enters the path via an air inlet optionally through an intake conduit. Air leaves the orbital path 3 in a centripetal direction through an air discharge system and an air outlet. The solid substance to be inhaled is provided, preferably in the form of a film, on the surface of the orbital path or on the surface of the ball. A user inhales through the air outlet 8, and this causes air to be drawn into the orbital path through the air inlet. This causes the ball to circulate around the orbital path, in which process solid substance is dislodged and caused to flow with the air out through the outlet.

16 Claims, 4 Drawing Sheets

INHALER

BACKGROUND OF THE INVENTION (1) Field of the Invention

This invention relates to an inhaler by means of which a solid substance in particulate form, in particular a pharmacologically active substance, can be introduced into the inhaled air of the user of the inhaler.

(2) Description of the Prior Art

Various types of such inhaler are known, one of which is disclosed in German Pat. No. 845385 (and equivalent U.K. Pat. No. 654860) granted to Abbott Laboratories. In the Abbott device a supply of solid material in the form of a fine powder is provided in a capsule having a mesh screen at the lower end. The capsule is adapted to be inserted into the device in such a manner that its lower part projects into a chamber communicating with an air inlet via an inlet tube bent to form approximately a semicircle. An air outlet is provided in the form of a mouthpiece or the like. A ball is located in the inlet tube and is moved during inhalation by the flow of the inhaled air towards the end of the inlet tube, whereby the ball strikes against the capsule and causes a small amount of solid material to fall through the screen of the capsule and to enter the airstream.

A major drawback of the device just described is that it is suitable only for dispensing a relatively large quantity of material, which means that the material in the capsule has to comprise a large amount of an inert carrier in addition to the active substance. This means that it requires many inhalations to transport such an amount of solid material, and it may take from 5 to 10 minutes for a user to inhale sufficient air to take in the required dose of the active substance. This is unacceptable in many cases, particularly where inhalation is intended to relieve conditions which require immediate treatment, such as the conditions prevailing in an asthmatic attack.

Furthermore, because of its shape, the device described above is rather unwieldy and is too large to be conveniently carried around in a bag or pocket. Finally, too much handling is required on the part of the user to prepare for use, i.e. insertion of the capsule into the device after removal of a cap sealing the screen (at which point there is a dnager of loss of solids through the scrren) and the need for correct positioning of the device during inhalation.

It should be mentioned at this point that some, though not all, of the disadvantages referred to above are shared by other forms of known inhaler. In particular, all inhalers presently on the market are relatively large in size and, as a consequence of their expense, all are intended for repeated use.

SUMMARY OF THE INVENTION

It is an object of the present invention to provide an inhaler of a design which is such that, if desired, it can be made much smaller than known inhalers and which is sufficiently simple and inexpensive that it may be used only once and then disposed of, and also to provide a device by means of which a uniform and reproducible dose may be dispensed.

According to the present invention there is provided an inhaler for introducing a solid substance in particulate form into the inhaled air of a user, comprising a body having a surface therein which defines an endless path. An air inlet and an air outlet communicating with said endless path to provide for air to flow from the inlet to the outlet via said path under the effect of inhalation by the user through said outlet, and a ball located in said path and arranged to circulate therearound under the effect of said air flow, said solid substance being provided on said body surface or on said ball.

Preferably the endless path which is referred to below as an orbital path, is at least approximately circular as viewed in plan. Also, the air outlet is preferably so arranged that air leaves the orbital path in a centripetal direction. The advantages of doing this are explained below.

In an embodiment of the invention the air inlet communicates with the orbital path via an air intake conduit which opens tangentially into the orbital path. Alternatively, however, the air inlet may open directly into the orbital path, in which case air will, of its own accord, enter the orbital path tangentially. The significance of tangential entry of air into the orbital path is that this helps to ensure laminar air flow within the orbital path, which is advantageous in terms of providing easy circulation of the ball. If the air were to enter non-tangentially this would be likely to give rise to turbulence and a less efficient driving effect on the ball.

Mention will now be made of the principles of operation of the device, as they are presently understood. It is to be appreciated, however, that the operation of the device is in no way dependent on the correctness of the explanation now put forward. Air is caused to enter the orbital path, preferably tangentially, by suction applied at the air outlet. This sets the ball in orbital motion, which movement of the ball gives rise to a spectrum of relative movements between the stationary surface of the orbital path and the surface of the ball rotating in every direction in space. These relative movements exert compressive and shear forces on the material on the ball surface, on the surface of the orbital path, or between the surfaces of the ball and the orbital path, which initiates a fragmentation process.

This is combined with a process of aerosol formation, whereby finely ground particulate material is dispersed into the air that leaves the orbital path via the air outlet, preferably centripetally.

It is convenient at this point to note the advantageous effect provided by having the outlet air flowing centripetally. Both the ball and particulate material circulating around the orbital path are subjected the centrifugal forces, whereas the air is forced to leave the path centripetally. This produces a mixing effect between the air and the particles, with the air inevitably carrying with it a certain proportion of the solid particles. It is further to be noted that the opposing centrifugal and centripetal forces acting on the particles give rise to a distinction between smaller and larger particles, with the smaller particles being more likely to be entrained by the air to flow centripetally, and the larger particles being less likely to be entrained. The larger particles thus tend to remain in the orbital path until they are reduced to a smaller size. A further, and quite distinct advantage of having outlet air flowing centripetally is that this tends to reduce the size of device and makes it easier to construct.

The inhaler according to the present invention permits small amount of active substances to be administered in accurate doses. It should therefore be unnecessary to dilute the active substance and thus rapid action can be achieved in a short time period.

The device does not require a separate cartridge or other container for the active substance, nor does it require specific positioning when in use, which makes it simple and safe to handle. Due to its almost immediate action it is suitable for use in emergency situations. The device can be simply constructed at low cost, which permits it to be used once and then disposed of.

Furthermore, the design of the inhaler allows production in a very small size, so that the inhaler may conveniently be carried by a user at any time.

Instead of one ball, two, three or even more balls may be provided in the orbital path. Additional balls provide additional areas of friction, thus improving the discharge of solids. This effect can be further enhanced if the balls have different diameters.

The diameter of the ball used is preferably from 2 to 7 mm, more preferably 3 to 5 mm, and most preferably about 4 mm. Where a plurality of balls is used the above diameter refers to the diameter of the larger or largest of the balls.

The solid material which is to be inhaled is preferably applied in the form of a film onto the surface of the ball and/or the surface of the orbital path. The surface of the ball and/or the surface of the orbital path are preferably not smooth, as this provides for a larger quantity of substance to be applied a simpler application of the substance, more rapid fragmentation of the film during use of the device, and better dispersion of the substance in the air during use.

In a preferred embodiment the body of the inhaler consists of a support in which are formed the orbital path, the tangential air intake circuit, (if one is provided) and an air discharge system which is centripetal relative to the orbital path, and a cover-sheet provided with the air inlet and the air outlet. In this embodiment the air inlet and the air outlet are preferably formed as simple, circular air passage openings in the cover sheet. In order to ensure conditions of low microbiological contamination up to the time when the device is used, the cover sheet is preferably itself covered by a pull-off film which closes the air inlet and air outlet. In order to prevent the film from retaining particles of solid material in the area of the inlet and outlet of the cover sheet, which particles may have come off the surfaces of the ball or orbital path during transport or handling, the film is preferably designed to be repellent to such particles in the area of the air inlet and outlet. For that purpose the film may be coated metal, preferably coated aluminium, with the metal on the side facing the air inlet and outlet. Alternatively, the film may be a wholly metal film, for example an aluminium film, or it may be a laminated film, for example composed of laminated films of paper and aluminium, or a film coated with a hydrophobic material such as polytetrafluoroethylene.

BRIEF DESCRIPTION OF THE DRAWING

The invention will now be further described with reference to the accompanying drawings, in which:

FIG. 1 is a diagrammatic representation in sectional elevation of a first embodiment of the device according to the invention, the body of which is composed of a support and a cover-sheet;

FIGS. 2 and 3 are top plan views of the support and cover-sheet of the device shown in FIG. 1;

FIG. 4 is an enlarged section along the line IV—IV of FIG. 2:

FIG. 5 is a sectional elevation, in exploded form, of a second embodiment of the device according to the invention;

FIGS. 6 and 7 are top plan views of the support and the cover-sheet of the device according to FIG. 5;

FIG. 8 is a diagrammatic sectional view of a prototype of the device according to the invention produced for text purposes and having an exchangeable insert body;

FIGS. 9 and 10 show the insert body of FIG. 8 in elevation and top view respectively;

FIGS. 11 and 12 are diagrams of two possible configurations of the orbital path of the inhaler, deviating from a circular form;

FIG. 13 is a perspective view of another embodiment having a mouthpiece; and

FIG. 14 is a top plan view of the support and cover-sheet of a further embodiment of the invention.

DETAILED DESCRIPTION OF PREFERRED EMBODIMENTS

The inhaler illustrated in FIGS. 1 to 3 has a body composed of a support 1 and a cover-sheet 2, the support 1 having a recess which defines in the body a toroidal, circular orbital path 3 for a ball 4. The support 1 has a further recess which defines an air intake conduit 5 opening into the orbital path 3. The conduit 5 communicates with a circular air passage opening 6 in the cover-sheet 2, which opening constitutes the air inlet of the device. The support 1 is further provided with an air discharge system 7 which provides communication between the orbital path 3 and a circular air passage opening 8 formed in the cover-sheet 2 and constituting the air outlet of the inhaler. A pull-off film 9 seals the inlet and outlet openings 6 and 8 in a sterile manner. It will be noted that the air intake conduit 5 is of smaller depth than the orbital path 3 so that the ball 4 is provided with sufficient mechanical guidance even in the area adjacent the opening of the conduit into the path. The active substance to be inhaled is preferably applied in the form of a film to the surface of the ball 4 and/or the surface of the orbital path 3 in a manner described in more detail below.

As shown in FIG. 4, the ball has a certain amount of play with respect to the surface of the path 3, this surface being provided partly by the inner surface of the support 1 and partly by a portion of the inner surface of cover-sheet 2. The amount of play determines the efficiency of the air propulsion of the ball and the extent to which the active substance is taken up by air leaving the orbital path. Due to suction of air occurring during inhalation at the air outlet 8, air enters the orbital path through the intake conduit 5 and propels the ball 4. As already indicated, because of the movement of the ball, compressive and shear forces are exerted between the surface of the ball and the surface of the orbital path, which serve in the first instance to remove particles of active substance from whichever of those surfaces it has been applied to, and then serve to grind or disperse those particles.

The fine particles are thereby distributed in the air that leaves the orbital path through the discharge system 7 and thence through the air outlet 8 to the user.

The centripetal air discharge system 7 is formed by the free space between the support 1 and the cover-sheet 2 in a central area 10 defined within the orbital path 3. In the embodiment of FIGS. 1 to 4 the air discharge system 7 is simply an annular clearance of uniform cross-section, the external diameter of which is the diameter D of the area 10 and the internal diameter of which is the diameter of the circulr air outlet 8.

Figure 1:
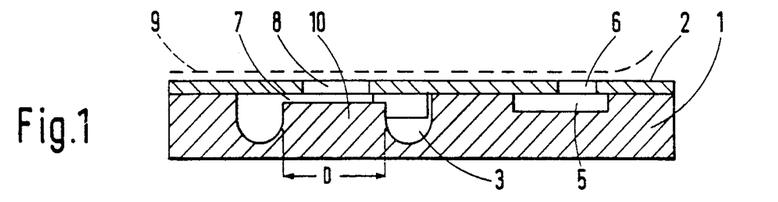
Figure 2:
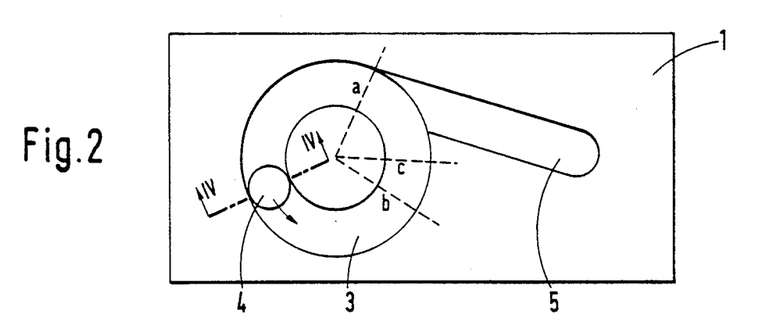
Figure 3:
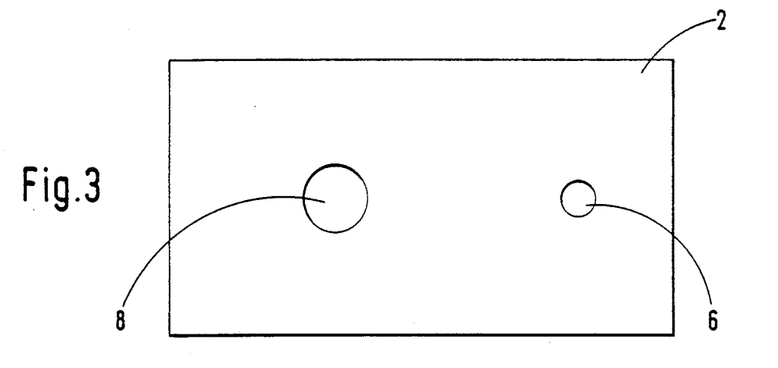

Efficiency in propulsion of the ball can be improved by giving the above mentioned annular clearance a non-uniform cross-section, such that the cross-section is a minimum immediately after entry of the intake circuit 5 into the orbital path (location a in FIG. 2) and increases steadily to reach a maximum immediately before the air intake conduit (location b in FIG. 2), before returning abruptly to a minimum (at location c in FIG. 2). Such a variation in the cross-section of the air discharge system 7 can be easily obtained by a spiral or serrated configuration of the central area 10 of the orbital path 3, as is explained below in more detail with reference to FIGS. 8 to 10.

Figure 4:
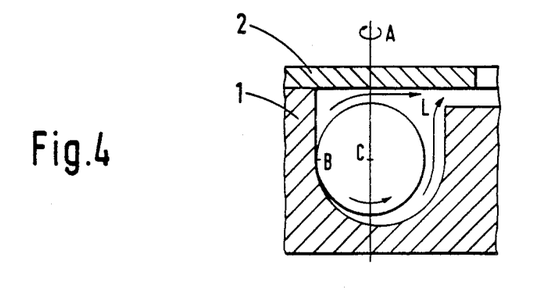
Figure 5:
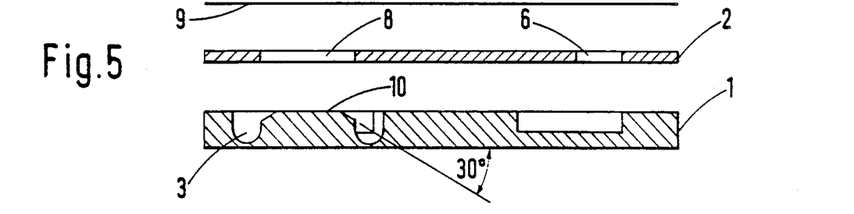
Figure 6:
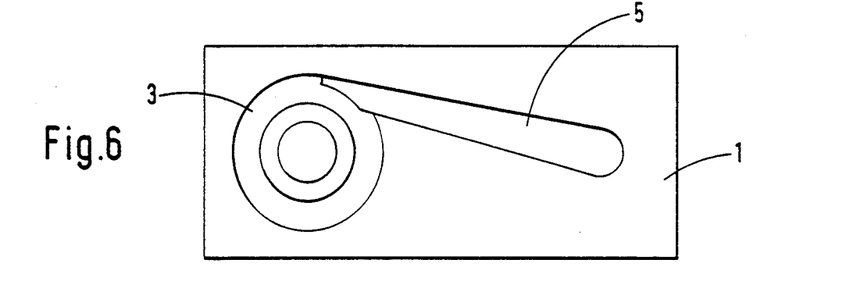
Figure 7:
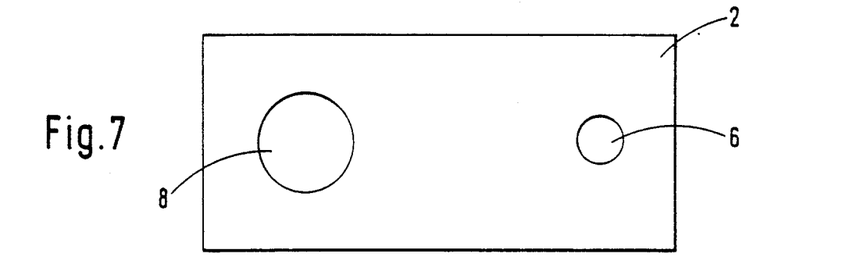

In the embodiment illustrated in FIGS. 5 to 7, the central area 10 has an upper frusto-conical portion with a cone angle of 120°. The upper surface of the frusto-conical portion is co-planar with the upper surface of the interface between the support 1 and the cover-sheet 2. The air outlet 8 has a diameter corresponding to the inner diameter of the orbital path 3, i.e. the diameter of the base of the frusto-conical portion of the central area 10, so as to form an annular clearance between the lower edge of the air outlet 8 of the cover-sheet 2 and the frusto-conical surface of the central area 10. As in the case of the embodiment of FIGS. 1 to 4 the air discharge system is provided by an annular clearance which is rotationally symmetrical, i.e. the annular clearance has the same cross-section at all points.

In a typical practical embodiment of the device shown in FIGS. 5 to 7, the length of the inhaler is 50 mm, the width 22 mm and the height 4.5 mm. The orbital path has a width of 3.1 mm and the glass ball used has a diameter of 3 mm. The diameter of the air outlet opening 8 is 10 mm, and the diameter of the air inlet opening 6 is 5 mm. Depending on the chosen pressure difference and the ball tolerance selected, the rotational speed of the ball is between 5 and 50 Hz, which corresponds to 300 to 3000 revolutions per minute. If, as is preferred, the ball diameter is 4 mm the width of the orbital path is preferably about 4.3 mm, with the other dimensions already mentioned being substantially the same. The same dimensional characteristics apply, in substance, to the embodiment of FIGS. 1 to 4.

It will be seen from the above discussion of dimensions that the device of the present invention can indeed be made extremely small, in contrast to presently available inhalers.

Figure 8:
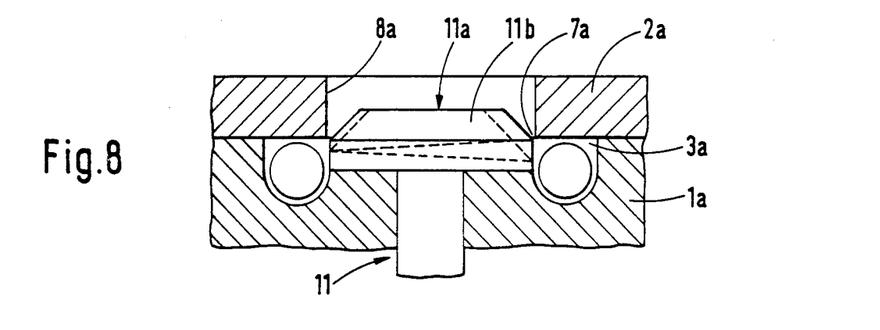

FIG. 8 shows part of a prototype of the inhaler according to the invention, composed of three aluminium elements. The three elements are a lower support body 1a with a circular orbital path 3a, an upper cover-plate 2a with a circular air passage 8a forming the air outlet and an exchangeable insert body 11, the top 11a of which constitutes the central area of the orbital path 3a. This prototype has been used to test various geometrical configurations of the central area of the orbital path.

As can be seen in FIG. 8, the frusto-conical path 11b of top 11a of the insert body 11 has a spiral form, by virtue of which the cross-section of the annular clearance 7a forming the centripetal air discharge system widens from a minimum immediately after the junction with the air intake conduit up to a maximum immediately before the air intake conduit.

Figure 9:
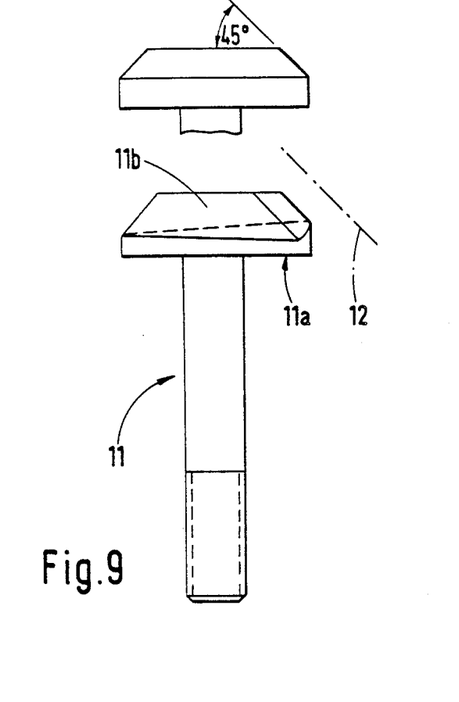
Figure 10:
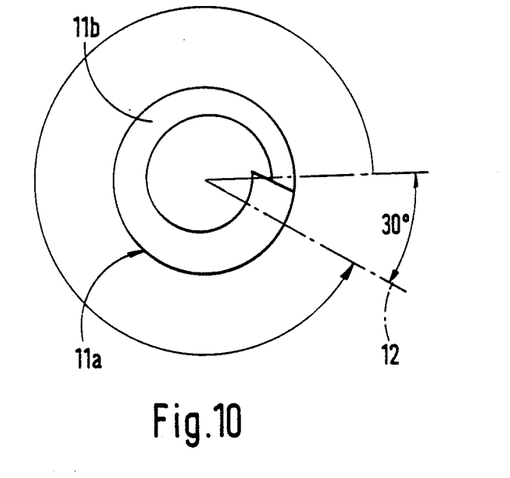
Figure 11:
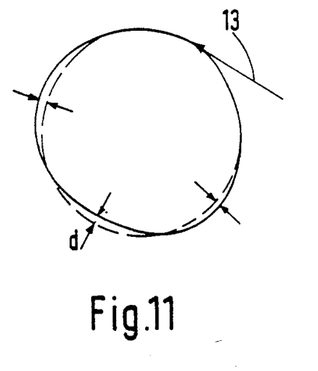
Figure 12:
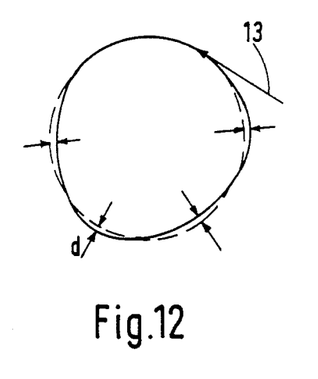

With reference to FIGS. 9 and 10, which show the insert body in elevation and top view, a brief description will now be given of the production of the spiral form mentioned above by means of an end-milling cutter. The insert body 11 starts with the shape illustrated in the upper portion of FIG. 9, that is to say, the top has a lower cylindrical portion surmounted by a frusto-conical portion having a cone angle of 90°. The insert body 11 is then slowly turned about its vertical axis and at the same time a milling cutter is slowly advanced towards the axis of rotation of the insert body. The milling cutter is a tool approximately 4 to 5 mm in diameter, and the axis of rotation of the milling cutter is denoted by reference numeral 12 in FIG. 9. The insert body 11 is rotated through an angle of 330° while the milling cutter advances, and this produces the spiral form shown in FIGS. 8 to 10.

As a result of the spiral form of the central area of the orbital path, the cross-section of the air discharge annular clearance is relatively small in the first propulsion phase of the ball, a phase which can be regarded as extending for about 120° from immediately after the opening of the air intake conduit into the orbital path. During this phase little air can flow out of the orbital path. Thereafter a second phase ensues during which the cross-section of the clearance becomes progressively wider so that more and more air can be discharged from the annular path. It will be appreciated that there is no definite division between the two phases, since the increased in the width of the annular clearance is continuous. During the first phase effective propulsion of the ball is achieved, the aim being to get as high a rotational speed for the ball as possible. During the second phase the ball continues to be propelled, but larger amounts of air are lost from the region ahead of the ball, the air taking with it particulate material to be inhaled. The second phase ensures that the desired amount of particulate material can be inhaled at an acceptably low suction pressure.

Figure 13:
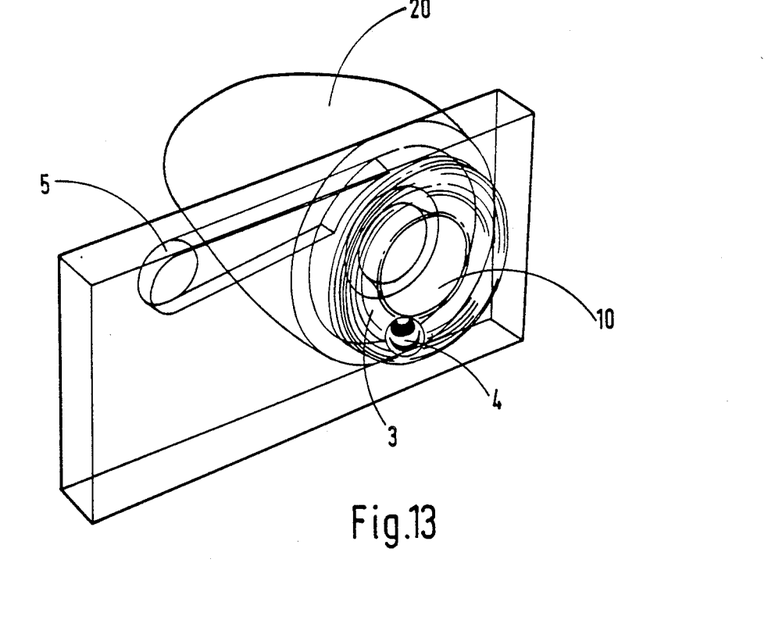

It has been found that an orbital path deviating slightly from a circular form may be useful, since periodic acceleration effects on the ball tend to result in improved removal of active substance from the surface of the ball and/or the surface of the orbital path, and in improved aerosol formation. Such periodic acceleration forces may be brought about by using an elliptical path, or by using a generally circular path with a plurality of convex or concave indentations, for example from two to four such indentations. In either case, deviations from the circular form should not be too great or else the braking effect on the ball will become too large. With elliptical paths an ellipticity coefficient of about 1.25 has proved to be suitable.

FIGS. 11 and 12 are diagrams illustrating two examples of circular paths with convex and concave indentations respectively. Arrow 13 indicates the direction of air intake into the orbital path. The deviation from the circular form marked with d may amount to about 1/25 of the diameter of the circular path.

The device according to the present invention may be used for inhalation either through the mouth or through the nose. In order to make the device easier to use an outlet member in the form of a mouthpiece or nosepiece, as the case may require, may be mounted on the cover sheet 2 to communicate with the air outlet opening 8. FIG. 13 is a perspective view of a device according to the invention having a mouthpiece, which is denoted by reference numeral 20. In other respects the device of FIG. 13 is broadly the same as that of FIGS.

5 to 7, and the same reference numerals are therefore used in FIG. 13 as in those Figures.

Figure 14:
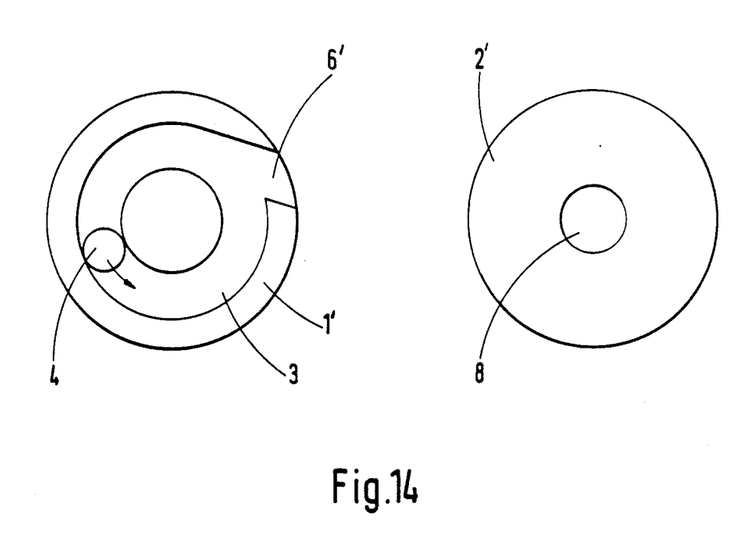

The provision of such an outlet member becomes particularly valuable in connection with the further embodiment of the invention which is shown in FIG. 14. In the embodiment of FIG. 14 the intake circuit 5 is omitted and air enters the orbital path 3 through an air inlet 6' provided in the support 1' rather than the cover-sheet 2'. The cover-sheet 2' contains only the air outlet 8. Both the support 1' and the cover-sheet 2' are reduced in size compared to the previously described embodiments, and are shown in FIG. 14 as being circular in form. This embodiment is so small that it is very desirable to include an outlet member in the form of a mouthpiece or nosepiece, to enable the device to be conveniently handled by a user.

The body of the inhaler according to the present invention, i.e. the support 1 or 1' and cover-sheet 2 or 2', may suitably be made of a plastics material, for example, ABS, the support being either an injection-moulded part formed from a plastics granulate, or a deep-drawn moulding formed of plastics sheeting which is heated and formed over a mould. Injection-moulding is presently preferred since that process allows for higher precision. Alternatively, the body of the inhaler may be formed from a metal, such as aluminium, the desired form being achieved by stamping or by deep-drawing.

The support and cover-sheet may be joined by a variety of methods, depending on the materials involved, including ultrasonic welding, anodic bonding, or adhesion. If adhesion is used the amount of adhesive, the pattern in which adhesive is applied and the contact pressure used must be such that penetration of the adhesive into the path of the ball is avoided.

The ball may be made of glass, metal, a plastics material, a ceramic material, for example alumina.

For reasons already mentioned, it is preferred that the surface of the ball and/or the surface of the orbital path, should be non-smooth. In the case of glass balls, a rough ground surface gives the desired effect, and permits good adhesion of the active substance when applied thereto by, wetting with a solution of the active substance and subsequent evaporation of the solvent. The manner of applying the active substance to the glass balls is described is more detail below. Alternatively, the ball may have a surface structure similar to that of a golf ball. If the surface of the orbital path is non-smooth, and possibly, the active substance applied also to the orbital path, the glass ball used may be acid-treated.

In addition to any surface characteristics which the surface of the orbital path may have to render it non-smooth, the orbital path surface preferably has helical grooves formed therein extending along the direction of movement of the ball, similar to the riflings in firearms. Contact of the ball with the grooved helical path causes the ball to spin perpendicular to the direction of travel. This is believed to be of particular advantage in relation to the dispersion of the active substance in the air. The helical grooves may be formed in the orbital path during the injection-moulding, deep-drawing, stamping or other process by which the support is formed.

The grinding and dispersing functions of the ball will become clearer on considering the dynamic behaviour of the travelling ball with reference to FIG. 4.

1. Under the influence of centrifugal force, the ball is in rolling contact with the outer annular wall of orbital path 3 (see point of contact B). This causes turning of the ball about axis A.

2. Helical grooving of the surface of the orbital path causes simultaneous turning of the ball, e.g. in the direction of the arrow, about axis C, which extends perpendicularly to the plane of the drawing.

3. The speed gradient between the surface for the ball and the surface of the orbital path continues to increase in the direction of arrows L, which represent the airflow towards the centripetal discharge system which, due to the acceleration forces on the particles, contributes to good particle/air distribution.

The inhaler according to the invention is suitable for the administration of any pharmacologically active substance that can be inhaled and is absorbed via the mucous membranes of the respiratory passages. In particular, the inhaler is designed for the treatment of asthma and bronchitis by means of the substances salbutamol, beclomethasone dipropionate, terbutaline and sodium cromoglycate.

There are several ways of introducing the active substance into the inhaler, and some of these will now be mentioned.

1. The active substance is dissolved in a solvent and the ball dipped into it. Upon evaporation of the solvent there remains a film of solid active substance.

2. A solution of active substance is introduced into the recess in the support which forms the orbital path. Upon drying a film of active substance remains in the recess.

3. After the complete device has been assembled, including the ball, the active substance is introduced in solution into the orbital path, and upon evaporation a film of active substance remains on the surface of the orbital path and may remain also on the surface of the ball.

4. The substance is introduced in solid form into the device after assembly. In this case the particulate material simply lies on the surface of the orbital path without being attached thereto as it is when it is present as a film.

If the active substance is applied in solution, and if the inhaler body is made of a plastics material, account may need to be taken of the possibility that the solvent used may interact with the plastics material, for example by dissolving but the plasticizer. If such an effect is anticipated the body of the inhaler can be subjected to a process of metal coating by vaporization to prevent it being attacked by the solvent.

Due to the rotation of the ball, the solid particles are finely ground or dispersed and have a diameter on leaving the inhaler such that a fraction of the particles in the range of 10 to 20 microns can be inhaled. The total quantity of active substance which needs to leave the inhaler will depend on the nature of the active substance itself and the dosage requirements. For example, for salbutamol, a typical dose is from 200 to 400 μg.

As already mentioned, a single inhaler may be provided with more than one ball. For example, where the orbital path has a width of 3.7 mm a pair of balls 3.5 and 3 mm in diameter may be used, and where the orbital path has a width of 4.3 mm a pair of balls 4.1 mm and 3.7 mm may be used. These dimensions are given by way of example only, and other dimensions could be used. In each case the larger ball is the one to which the air provides the main propulsive force. The smaller ball being propelled mainly by impact with the larger ball. Where two balls are used both can carry the same active substance, but an alternative possibility is that each may carry a different active substance. For example, it is sometimes necessary for salbutamol and beclomethasone dipropionate to be administered together, in which case one of the balls may be coated with one of these substance and the other ball may be coated with the other.

One further possibility afforded by the use of a plurality of balls is that one of the balls may consist purely of the active substance, or a mixture of active substance and an inert carrier, rather than having the active substance merely as a coating on an inert substrate such as glass. In this case the other ball or balls may carry active substance or may consist purely of the inert substrate in this case the ball of pure drug would not be the largest of the balls so that the main propulsive force would be applied to the other ball, or one of the other balls, as the case may be.

Some examples will now be given of compositions used to coat salbutamol onto glass balls by the solvent method referred to above. The compositions are given in terms of percentage by weight.

| Composition 1 | |
| --- | --- |
| Glass balls 4 mm | 59.95 |
| Salbutamol | 0.08 |
| Ethanol | 39.97 |
| Composition 2 | |
| Glass balls 4 mm | 57.49 |
| Salbutamol | 0.08 |
| Ethanol | 42.43 |
| Composition 3 | |
| Glass balls 4 mm | 59.37 |
| Salbutamol | 0.08 |
| Polyvinylpyrrolidone | 0.008 |
| Ethanol | 40.542 |
| Composition 4 | |
| Glass balls 4 mm | 98.96 |
| Salbutamol | 0.17 |
| Ethanol | 0.87 |
| Composition 5 | |
| Glass balls 3 mm | 95.34 |
| Salbutamol | 0.58 |
| Polyvinylpyrrolidone | 0.58 |
| Ethanol | 3.50 |
| Composition 6 | |
| Glass balls 4 mm | 82.22 |
| Salbutamol | 1.49 |
| Polyvinylpyrrolidone | 1.49 |
| Ethanol | 14.80 |
| Composition 7 | |
| Glass balls 4 mm | 53.91 |
| Salbutamol | 0.09 |
| Ethanol | 46.00 |
| Composition 8 | |
| Glass balls 4 mm | 95.71 |
| Salbutamol | 0.12 |
| Polyvinylpyrrolidone | 0.07 |
| Ethanol | 4.10 |
| Composition 9 | |
| Glass balls 3 mm | 91.95 |
| Salbutamol | 0.56 |
| Polyvinylpyrrolidone | 0.09 |
| Ethanol | 7.40 |
| Composition 10 | |
| Glass balls 4 mm | 59.91 |
| Salbutamol | 0.15 |
| Ethanol | 39.50 |
| Distilled water | 0.40 |
| Glycerin | 0.04 |
| Composition 11 | |
| Glass balls 4 mm | 59.66 |
| Ethanol | 39.73 |
| Distilled water | 0.40 |
| Glycerin | 0.06 |
| Salbutamol | 0.15 |
| Composition 12 | |
| Glass balls 4 mm | 57.31 |

| -continued | |
| --- | --- |
| Salbutamol | 0.15 |
| Xylitol | 1.73 |
| Distilled water | 2.60 |
| Ethanol | 37.78 |
| Distilled water | 0.38 |
| Glycerin | 0.05 |
| Composition 13 | |
| Glass balls 4 mm | 73.03 |
| Salbutamol | 0.18 |
| Xylitol | 1.70 |
| Distilled water | 2.64 |
| Ethanol | 22.00 |
| Distilled water | 0.22 |
| Glycerin | 0.23 |

Notes

1. In the case of compositions 10 to 13, glycerin serves as an adhesive to improve retention of salbutamol on the balls.

2. Xylitol, included in compositions 12 and 13, also serves as an adhesive.

3. The distilled water referred to in compositions 10 and 11, and the second mentioned quantity of distilled water referred to in compositions 12 and 13, serves as a plasticiser for the salbutanol. The first mentioned quantity of distilled water in compositions 12 and 13 serves as a solvent for the xylitol.

4. In the case of compositions 1 to 11, salbutamol alone, or with an adhesive, was dissolved in ethanol, and this solution was sprayed onto the glass balls rotating in a coating pan by means of a hand-held spray gun. The coated balls were dried at 40° C. by means of a hot-air blower. In the case of compositions 12 and 13, the solution of xylitol in distilled water was sprayed onto the balls before the solution of salbutamol and adhesive was similarly applied.

The solvent used for applying a film of active substance to the balls or orbital path will of course depend on the nature of the active substance. For example, where the active substance is beclomethasone dipropionate the solvent may be chloroform, methylene chloride, dichloroethane, acetone, methanol, ethanol, ethyl acetate or methyl isobutyl ketone.

We claim:

1. An inhaler for introducing a solid substance in particulate form into the inhaled air of a user, comprising (a) a body having (1) an internal surface defining an endless path, (2) an intake conduit for the inhaled air, the air intake conduit opening tangentially into said endless path, and (3) an air outlet adapted for fluid communication with a breathing passage of the user and discharge means for the inhaled air in fluid communication with said endless path and the air outlet, and said air outlet and discharge means being disposed centripetally relative to the endless path whereby inhalation by the user through the outlet causes air to flow through the air intake conduit, the endless path and the discharge means to the outlet, (b) a ball having a surface and being disposed in said endless path, the ball being arranged in said endless path to circulate therearound under the effect of the air flow, and (c) a solid medicament substance distributed between the surface of the endless path and the ball.

2. The inhaler according to claim 1, wherein the solid substance is distributed over the surface of the endless path.

3. The inhaler according to claim 1, wherein the solid substance is distributed over the surface of the ball.

4. The inhaler according to claim 1, wherein the solid substance is distributed over the surfaces of the endless path and the ball.

5. The inhaler according to claim 1, wherein said body comprises a support and a cover sheet on said support, the support defining a first recess which constitutes said internal surface and a second recess defining the intake conduit for the inhaled air, and the cover sheet overlying the recesses and defining an air inlet fluidically communicating with the second recess and the air outlet.

6. An inhaler according to claim 5, wherein said air inlet and said air outlet have the form of circular openings in the cover sheet.

7. An inhaler according to claim 6, wherein a film is removably secured to the cover sheet to close said circular openings.

8. An inhaler according to claim 7, wherein the film is a metal foil.

9. An inhaler according to claim 7, wherein the film is a laminated film composed of a paper film and an aluminium film, the latter film being located on the side facing said circular openings.

10. The inhaler according to claim 5, wherein the portion of the support disposed centripetally relative to the endless path is sized and shaped to define an annular clearance between the support and the cover sheet, and said annular clearance comprises said air discharge means.

11. The inhaler according to claim 10, wherein the annular clearance has a cross-section increasing in the direction of circulation of the ball from a minimum at a point immediately after the air intake conduit opens into said endless path to a maximum immediately prior to said point.

12. The inhaler of claim 11, wherein said portion of said support disposed centripetally relative to the endless path has a spiral surface defining the increasing cross-section of the annular clearance.

13. An inhaler according to claim 1, wherein said path is circular in shape.

14. An inhaler according to claim 13, wherein said circular path in diametrical view, has from 2 to 4 indentations, with a maximum deviation from the circular path of approximately 1/25 of the diameter of the circular path.

15. The inhaler according to claim 1, wherein at least one of the surfaces is rough.

16. The inhaler according to claim 1, wherein said body comprises a support and a cover sheet on said support, the support defining a first recess which constitutes said internal surface and a second recess extending to the periphery of the support and defining the intake conduit for the inhaled air, and the cover sheet overlying the recesses and defining the air outlet.

* * * * *